(12) United States Patent
Atanasoska et al.

(10) Patent No.: US 8,507,639 B2
(45) Date of Patent: Aug. 13, 2013

(54) RADIOPAQUE AMIDE POLYMERS AND MEDICAL DEVICES FORMED THEREOF

(75) Inventors: Liliana Atanasoska, Edina, MN (US); Scott Schewe, Eden Prairie, MN (US); Robert Warner, Woodbury, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1503 days.

(21) Appl. No.: 11/519,139

(22) Filed: Sep. 11, 2006

(65) Prior Publication Data

US 2008/0064848 A1    Mar. 13, 2008

(51) Int. Cl.
*C08G 69/08* (2006.01)

(52) U.S. Cl.
USPC ............ 528/310; 525/218; 525/296; 525/926; 604/103; 623/1.13

(58) Field of Classification Search
USPC .................. 623/1, 1.13; 525/218, 296, 328, 525/329, 926; 528/310; 604/103
See application file for complete search history.

(56) References Cited

U.S. PATENT DOCUMENTS

| | | | | |
|---|---|---|---|---|
| 3,287,324 | A | 11/1966 | Sweeny | 260/78 |
| 3,671,542 | A | 6/1972 | Kwolek | 260/30.8 |
| 6,677,473 | B1 | 1/2004 | Madison et al. | 560/52 |
| 2005/0106119 | A1 | 5/2005 | Brandom et al. | 424/78.08 |
| 2005/0187602 | A1* | 8/2005 | Eidenschink | 623/1.11 |
| 2006/0024266 | A1 | 2/2006 | Brandom et al. | 424/78.17 |
| 2006/0034769 | A1 | 2/2006 | Kohn et al. | 424/9.45 |
| 2006/0036316 | A1 | 2/2006 | Zeltinger et al. | 623/1.49 |
| 2006/0165926 | A1* | 7/2006 | Weber | 428/35.2 |
| 2006/0230476 | A1 | 10/2006 | Atanasoska et al. | 977/933 |

FOREIGN PATENT DOCUMENTS

| | | |
|---|---|---|
| DE | 19521940 | 12/1996 |
| EP | 1702914 | 9/2006 |
| WO | WO 93/10824 | 6/1993 |
| WO | WO 98/36013 | 8/1998 |

OTHER PUBLICATIONS

International Search Report dated Jan. 15, 2008 for PCT/US2007/018131claiming priority to U.S. Appl. No. 11/519,139.
eps@ce.net machine translation of DE 19521940.
eps@ce.net machine translation of WO 9310824 (with claims from EP 0616538 B1).
I. In, et al, "Soluble wholly aromatic polyamides containing unsymmetrical pyridyl ether linkages," Polymer 47 (2006) 547-55.
N. James, et al, "Polyurethanes with radiopaque properties," Biomaterials 27 (2006) 160-166.
F. Mottu, et al, "Iodine-containing cellulose mixed esters as radiopaque polymers for direct embolization of cerebral aneurysms and arteriovenous malformations," Biomaterials 23 (2002) 121-131.
Zoppi, et al, "Hybrids of Poly(ethylene oxide-b-amide-6) and ZrO2 Sol-gel: Preparation, Characterization, and Application in Processes of Membranes Separation," Advances in Polymer Technology, vol. 21, No. 1, (2002) 2-16.
Zoppi, et al., "Hybrids of poly(ethylene oxide-co-epichlorhydrin) and silica: phase separation, morphology and thermal properties," Polymer, vol. 39, No. 25, (1998) 6195-6203.
Zoppi, et al. "Hybrid films of poly(ethylene oxide-b-amide-6) containing sol-gel silicon or titanium oxide as inorganic fillers: effect of morphology and mechanical properties on gas permeability," Polymer 41 (2000) 5461-5470.
International Search Report dated Jan. 15, 2008 for PCT/US2007/018131claiming priority to U.S. Appl. 11/519,139.

\* cited by examiner

*Primary Examiner* — Gregory Listvoyb
(74) *Attorney, Agent, or Firm* — Vidas, Arrett & Steinkraus, P.A.

(57) ABSTRACT

Radiopaque polymers have a main chain and a plurality of amide groups which have bound to the amide nitrogen atom thereof an organohalide group that is pendant to the polymer main chain, the organo halide group including one or more iodine and/or bromine atoms thereon. The polymer may be a modified polyamide polymer, copolymer or block copolymer or a modified poly(meth)acrylamide or (meth)acrylamide copolymer or block copolymer. The polymers may be employed in medical devices and are useful for instance to track the movement of a catheter through the body or the inflation of a balloon at a site. The polymers may be made by coupling reactions performed on preexisting amide polymers.

9 Claims, No Drawings

RADIOPAQUE AMIDE POLYMERS AND MEDICAL DEVICES FORMED THEREOF

BACKGROUND OF THE INVENTION

Polymers that have been used to form medical device components include various amide polymers such as polyamides, polyether-block-amides and (meth)acrylamide polymers and copolymers. Amide polymers are typically substantially radiolucent, that is they have little or no opacity to X-rays and other high energy radiation sources. In medical device applications it would be desirable if these materials can be rendered more radiopaque, so that they can be more easily monitored in the body, for instance to track the movement of a catheter through the body or the inflation of a balloon at a site, or the like.

SUMMARY OF THE INVENTION

In one aspect the invention pertains to polymers having a main chain and a plurality of amide groups wherein at least some of the amide groups have, bound to the amide nitrogen atom thereof, an organohalide group that is pendant to the polymer main chain, the organo halide groups comprising one or more iodine and/or bromine atoms thereon. In at least some embodiments of the invention the iodine and/or bromine atoms in the organohalide groups provide enhanced radiopacity to the polymers.

The amide groups may be part of the main polymer chain or located entirely in a side chain to the polymer main chain. In some particular embodiments the polymer of the invention may be a modified polyamide polymer, copolymer or block copolymer or a modified poly(meth)acrylamide or (meth)acrylamide copolymer or block copolymer and/or the organohalide groups have at least two bromine or iodine atoms, for instance three or more bromine or iodine groups thereon. Exemplary of such organohalide groups include iodoarylcarboxyl groups having 2 or more iodine atoms on one or more aromatic rings, for instance 3, 4 or 5 iodine atoms.

A further aspect of the invention pertains to medical devices comprising a component formed of a polymer as described herein.

Still further aspects of the invention pertain to methods for making such polymers by coupling reactions performed on preexisting amide polymers and to ceramic/polymer hybrid composite materials comprising the inventive polymers.

These and other aspects of the invention are described more fully in the detailed description and claims which follow.

DETAILED DESCRIPTION OF THE INVENTION

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

Polymers that may be modified in accordance with the invention include polyamide polymers and copolymers and block copolymers which include at least one polyamide segment, as well as (meth)acrylamide homopolymers and copolymers.

Polyamide polymers have amide groups in the main chain of the polymer. In general polyamide polymers and copolymers include repeating groups of formula (I) or (II) or a combination thereof:

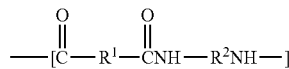

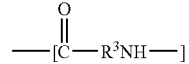

where $R^1$ taken with the carboxyl groups to which it is attached is a residue of a dicarboxylic acid, $R^2$ taken with the nitrogen atoms to which it is attached is the residue of a diamine, $R^3$, taken with the carboxyl and nitrogen atom to which it is attached is a residue of a aminoacid. $R^1$, $R^2$ and $R^3$ may be for instance divalent aromatic or aliphatic hydrocarbon groups or a mixed alkyl and aryl hydrocarbon group such as an alkarylene or aralkylene group. Aliphatic hydrocarbon groups include saturated and unsaturated hydrocarbons and linear branched and cyclic structures. Suitably $R^1$, $R^2$ and $R^3$ have from about 2 to about 20 carbon atoms. Optionally the groups $R^1$ $R2$ and $R^3$ may be substituted, for instance by halogen or interrupted by ether oxygen groups. In the case of copolymers multiple $R^1$, $R^2$ and/or $R^3$ groups of different structure may be present.

Specific examples of polyamide polymers are nylon-6, nylon-6,6, nylon-4,6, nylon-6,3, nylon-4,6, nylon-7, nylon-6, 10, nylon-6,12, nylon-10, nylon-11, nylon-12, and partially aromatic nylons, such as Grivory® resins and nylon-MXD6. Further examples include the aramids (aromatic polyamides), such as poly-meta-phenyleneisophthalamide (Nomex®, U.S. Pat. No. 3,287,324) or poly-para-phenyleneterephthalamide (Kevlar®, U.S. Pat. No. 3,671,542). The polyamide polymer may have pyridine groups in its structrure, for instance as described in I. In, et al, "Soluble wholly aromatic polyamides containing unsymmetrical pyridyl ether linkages," Polymer 47 (2006) 547-552.

The polyamide polymers may be obtained, for instance, by polymerizing various precursors having amino groups and carboxylic acid groups. Such precursors include, for example, monoaminomonocarboxylic acids; lactams of monoaminomonocarboxylic acids; diamines having at least 2 carbon atom between amino groups and dicarboxylic acids; and the like; and combinations thereof. Examples of monoaminomonocarboxylic acids or lactams thereof include aminocaproic acid, butyrolactam, pivalolactam, caprolactam, capryl-lactam, enantholactam, undecanolactam, dodecanolactam, and 3-aminobenzoic acid, 4-aminobenzoic acid, and the like. Examples of diamines include trimethylenediamine, tetramethylenediamine, pentamethylenediamine, octamethylenediamine, hexamethylenediamine, trimethyl hexamethylene diamines, meta-phenylene diamine, para-phenylene diamine, metaxylylene diamine, 2,2-bis-(p-aminocyclohexyl) propane, 2-methyl pentamethylene diamine, 4,4'-diaminodicyclohexylmethane, and the like. The dicarboxylic acids may be aromatic, for example, isophthalic and terephthalic acids, or aliphatic such as sebacic acid, octadecanedoic acid, suberic acid, glutaric acid, pimelic acid, adipic acid, azelaic acid, and the like. Instead of a dicarboxylic acid, a functional derivative thereof such as, for example, an ester an acid anhydride or an acid chloride may also be used.

The polyamide polymer may also be a polyamidoamine dendrimer, a polyamide-polyimide, a protein or peptide, for instance natural or synthetic silk protein.

The polyamide block copolymers have a main chain with at least one polyamide segment and at least one polymeric segment of a second polymer, such as a polyether or polyester. Examples of such block copolymers are polyether-blockamide copolymers (PEBA) which have polyamide and polyether blocks. The polyamide segments of the PEBA polymers may be based on aliphatic polyamides, aromatic polyamides or partially aromatic polyamides. The PEBA polymer can have a hardness in the range of 25 to 72 on the Shore D scale. The PEBA polymer may exhibit a flex modulus in a range of 23,000 to 125,000 pounds per square inch. The polyamide and polyether segments of these block copolymers may be linked through amide linkages, or through ester linkages as is the case of Pebax® polymers.

The generalized chemical formula for the Pebax® polymers may be represented by the following formula:

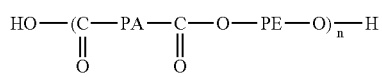

in which PA is a polyamide segment, PE is a polyether segment and the repeating number n is typically between 5 and 10. The polyamide segments are suitably aliphatic polyamides, such as nylon-12, nylon-11, nylon-9, nylon-6, nylon-6,12, nylon-6,11, nylon-6,9, or nylon-6,6. The polyamide segments may have a number average molecular weight in the range of 500-8,000, for instance 2,000-6,000, or 3,000-5,000.

The PEBA polymer may have one or more polyether blocks are which are aliphatic polyethers having at least 2 and no more than 10 linear saturated aliphatic carbon atoms between ether linkages. For instance the ether segments may have 4-6 carbons between ether linkages, such as poly(tetramethylene ether) segments. Examples of other polyethers which may be employed in place of the preferred tetramethylene ether segments include polyethylene glycol, polypropylene glycol, poly(trimethylene ether), poly(pentamethylene ether) and poly(hexamethylene ether). The hydrocarbon portions of the polyether may be optionally branched. An example is the polyether of 2-ethylhexane diol. The molecular weight of the polyether segments may suitably be between about 200 and 2,500, for instance between 250 and 1000.

The structural formula of the repeat units or (meth)acrylamide polymers is as shown:

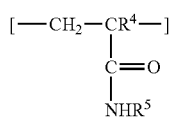

where $R^4$ and $R^5$ are independently H or methyl. The amide groups of (meth)acrylamide polymers is pendant to the main chain. Homopolymers and copolymers between (meth)acrylamide monomers and/or with other ethylenically unsaturated monomers such as olefin monomers, (meth)acrylate esters, and the like may be employed in the invention.

Modification of the amide polymers described above may be made by providing such polymers with organohalide groups comprising a one or more iodine and/or bromine atoms bound to the polymer by reaction with NH groups of the main chain or pendant amide moieties. The organohalide group may be linked to the amide nitrogen by a C—N bond and may include other hetero atoms in its structure. In some embodiments of the invention the organohalide groups have at least two iodine and/or bromine atoms thereon, for instance 3, 4 or 5 iodine or bromine atoms. In some embodiments the iodine or bromine atoms are substituents on one or more aromatic rings, for instance iodoarylcarboxyl groups of various structures may be provided including structures in which the carboxyl group is directly linked to an aromatic ring (e.g. a benzoyl group) or spaced by an intervening hydrocarbon group (e.g. a phenylacetyl group or phenylpropionyl group).

In some embodiments of the invention modification of a polymer having a plurality of amide groups with at least one hydrogen atom bound to the nitrogen atoms thereof may be accomplished in a coupling reaction with an iodine or bromine containing carboxylic acid, or an acid anhydride or acid chloride thereof. In some embodiments the carboxylic acid employed in the modification reaction includes one or more aromatic rings substituted with iodine or bromine atoms. Exemplary of such carboxylic acids are bromoacetic acid, iodoacetic acid, 2-bromopropionic acid, 3-bromopropionic acid, 2-iodopropionic acid, 3-iodopropionic acid, 2-iodobenzoic acid, 3-iodobenzoic acid, 4-iodobenzoic acid, 2-bromobenzoic acid, 3-bromobenzoic acid, 4-bromobenzoic acid, dibromoacetic acid, tribromoacetic acid, diiodoacetic acid, triidodoacetic, 2,3-dibromopropionic acid, 3,3-diiodopropionic acid, 3,3,3-triiodopropionic acid, 2,4,6-triiodobenzoic acid, 3,4,5-triiodobenzoic acid, 2,3,5-triiodobenzoic acid, tetrabromophthalic acid, tetraiodophthalic acid, 2,4,5,6-tetraiodobenzoic acid, pentaiodobenzoic acid, N-(2,6-diiodocarboxyphenyl)-3,4,5-triiodobenzamide as described in N. James, et al, "Polyurethanes with radiopaque properties," Biomaterials 27 (2006) 160-166, i.e.

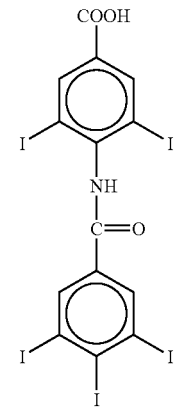

and various carboxylic acid compounds having multiple iodo and/or bromo groups described in U.S. Pat. No. 6,677,473, such as:

3,3',5,5'-tetraiodothyroacetic acid, i.e.,

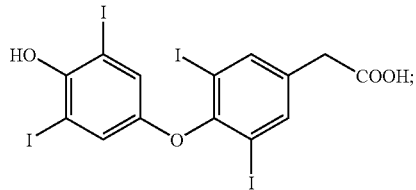 [SMILES: O=C(O)Cc1cc(I)c(Oc2cc(I)c(O)c(I)c2)c(I)c1]

3,3,5,5'-tetraiodothyropropionic acid, i.e.,

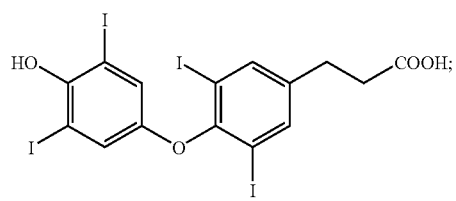 [SMILES: O=C(O)CCc1cc(I)c(Oc2cc(I)c(O)c(I)c2)c(I)c1]

3,3',5-triiodothyroacetic acid, i.e.,

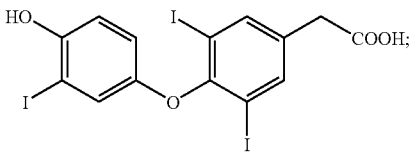 [SMILES: O=C(O)Cc1cc(I)c(Oc2ccc(O)c(I)c2)c(I)c1]

3,3',5-triiodothyropropionic acid, i.e.,

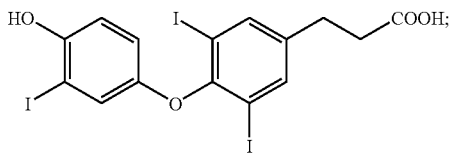 [SMILES: O=C(O)CCc1cc(I)c(Oc2ccc(O)c(I)c2)c(I)c1]

3,5-diiodothyropropionic acid, i.e.,

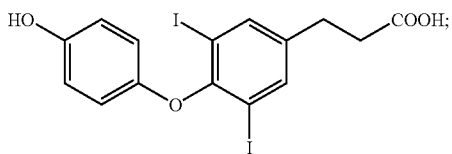 [SMILES: O=C(O)CCc1cc(I)c(Oc2ccc(O)cc2)c(I)c1]

3,5-diiodo-4-(3-bromobenzyloxy)benzoic acid, i.e.,

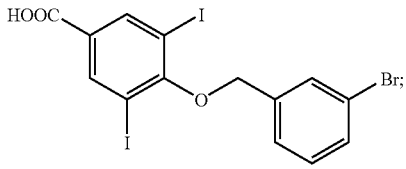 [SMILES: O=C(O)c1cc(I)c(OCc2cccc(Br)c2)c(I)c1]

3-(3,5-diiodo-4-(3-iodobenzyloxy)phenyl)propionic acid, i.e.,

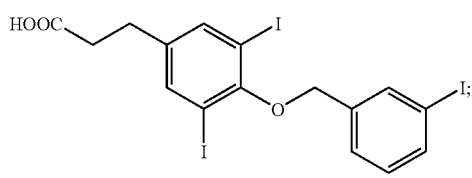 [SMILES: O=C(O)CCc1cc(I)c(OCc2cccc(I)c2)c(I)c1]

3,5-diiodo-4-(3-iodobenzyloxy)benzoic acid;
3,5-diiodo-4-(4-iodobenzyloxy)benzoic acid;
3,5-diiodo-4-(benzyloxy)benzoic acid;
3,5-diiodo-4-(2-bromobenzyloxy)benzoic acid;
3,5-diiodo-4-(4-bromobenzyloxy)benzoic acid;
3,5-diiodo-4-(2-methylbenzyloxy)benzoic acid;
3,5-diiodo-4-(3-methylbenzyloxy)benzoic acid;
3,5-diiodo-4-(4-methylbenzyloxy)benzoic acid;
3,5-diiodo-4-(4-tert-butylbenzyloxy)benzoic acid;
3,5-diiodo-4-(naphth-2-ylmethoxy)benzoic acid;
3,5-diiodo-4-(biphen-2-yloxy)benzoic acid;
3,5-diiodo-4-(3-methoxybenzyloxy)benzoic acid;
3,5-diiodo-4-(3-trifluoromethylbenzyloxy)benzoic acid;
3,5-diiodo-4-(3-trifluoromethoxybenzyloxy)benzoic acid;
3,5-diiodo-4-(3-fluorobenzyloxy)benzoic acid;
3,5-diiodo-4-(2,3,4,5,6-pentafluorophenyl-methoxy)benzoic acid;
3-(3,5-diiodo-4-(4-iodobenzyloxy)phenyl)propionic acid;
3-(3,5-diiodo-4-(benzyloxy)phenyl)propionic acid;
3-(3,5-diiodo-4-(3-bromobenzyloxy)phenyl)propionic acid;
3,5-dibromo-4-(3-iodobenzyloxy)-benzoic acid;
3-(3,5-diiodo-4-(4-bromobenzyloxy)phenyl)propionic acid;
3-[3,5-diiodo-4-(3-iodo-benzyloxy)-phenyl]-propionic acid;
3,5-dibromo-4-(4-tert-butyl-benzyloxy)-benzoic acid;
[3,5-diiodo-4-(3-iodo-benzyloxy)-phenyl]-acetic acid;
[3,5-diiodo-4-(4-iodo-benzyloxy)-phenyl]-acetic acid;
(4-benzyloxy-3,5-diiodo-phenyl)-acetic acid;
[4-(3-bromo-benzyloxy)-3,5-diiodo-phenyl]-acetic acid;
4-(2-nitro-benzyloxy)-3,5-diiodo-benzoic acid;
4-(3-nitro-benzyloxy)-3,5-diiodo-benzoic acid;
4-(4-nitro-benzyloxy)-3,5-diiodo-benzoic acid;
4-(2-cyano-benzyloxy)-3,5-diiodo-benzoic acid;
4-(3-cyano-benzyloxy)-3,5-diiodo-benzoic acid; and
4-(4-cyano-benzyloxy)-3,5-diiodo-benzoic acid.

The polymer amide groups, by such modification, may be transformed into an imide group in which at least one of the imide carbonyl groups is in a pendant location relative to the main chain of the polymer and includes an organohalide moiety linked thereto and the nitrogen atom of such imide group as well as the second carbonyl group thereof are either in the main chain of the polymer or a side chain, depending on the original location of the polymer amide group. For purposes of this application such imide groups are considered to be amide groups having bound to the amide nitrogen atom thereof, an organohalide group that is pendant to the polymer main chain.

In some cases the iodine or bromine functionalized carboxylic acid may be sufficiently reactive to provide satisfactory modification of the amide polymer by direct reaction. However, in general conversion of the carboxylic acid to acid chlorides is recommended. In some cases use of an anhydride of the carboxylic acid may provide results similar to those obtained with the acid chlorides. An exemplary procedure for forming acid chlorides using thionyl chloride, is described in N. James, et al, "Polyurethanes with radiopaque properties," Biomaterials 27 (2006) 160-166. A coupling reaction of the acid chloride with the amide functional polymer may be accomplished in a manner analogous to that described in the same document for functionalizing polyurethane polymers.

Suitably the coupling reaction is performed in a solvent that allows for a reaction temperature of about 120° C. or higher, for instance about 140° C. or higher, or 150° C.-170° C. A suitable such solvent is N,N-dimethylacetamide (DMAC) which can be refluxed at about 163° C. The polymer may be dried prior to the coupling, for instance by subjecting it to reduced pressure for a period of several hours, for instance 4-24 hours or by storing in a dessicator for several days. The solvent for the coupling reaction is also suitably distilled and dried prior to use. To reduce polymer degradation during the coupling reaction it may be useful in some instances to blanket the reaction with a dry inert gas such as nitrogen or argon.

Alternative coupling reactions may be employed starting from an amide polymer which has a hydroxyalkyl group bound to the nitrogen atom of the amide groups. The amide groups may be located within the main chain of the polymer or in a side chain amide group. Any of the acids listed above, or their acid chlorides, may be used in an esterification reaction with such hydroxyalkyl groups to produce organohalide substituted amide polymers in accordance with the invention. Esterification of hydroxyalkyl groups can go through a tosylate intermediate in the manner described for preparation of cellulose esters in F. Mottu, et al, "Iodine-containing cellulose mixed esters as radiopaque polymers for direct embolization of cerebral aneurysms and arteriovenous malformations," Biomaterials 23 (2002) 121-131, and such tosylate intermediates can also be used to accomplish conversion of the hydroxyalkyl groups to iodoalkyl groups as described in the same document. Conversion of hydroxyalkyl groups to bromoalkyl groups can be accomplished in a similar manner.

In general it may be expected that iodine atom substitution will provide more effective radiopacity than bromine atoms. Further it may be expected that radiopacity will increase as the degree of coupling of the organohalide groups to the amide groups of the polymer increases and/or as the number of iodine and/or bromine atoms per organohalide group is increased. These factors favor the use of organohalide groups with a plurality iodine or bromine atoms thereon. To the extent maximization of radiopacity is desired it will generally be desirable to employ organo halide groups with three or more iodine or bromine atoms, for instance 3, 4 or 5 such atoms, especially those in which the halide is iodine and those where there are four or more iodine atoms. In some cases however it may be that use of such groups will reduce the efficiency of the coupling reaction, so that better radiopacity might be obtained by using groups with lower halide content but which achieve greater degree of substitution on the amide polymer. Other factors may also influence the selection of the organohalide group for a particular application, including availability of the coupling agent, shelf-life, influence on particular physical properties of the polymer, biocompatibility, and the like.

In a specific illustrative embodiment nylon-12 (0.5 g) may be dissolved in 10 ml DMAC in a 50 ml R.B. flask. 3,4,5-Triiodobenzoic acid chloride (0.5 g) dissolved in 10 ml DMAC is then added and the mixture refluxed at 163° C. for 12-24 hrs. The polymer may then be concentrated, precipitated with methanol, and dried. The resulting polymer will have pendant iodoarylcarboxyl groups of the structure:

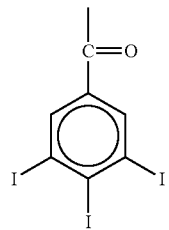

bound to nitrogen atoms of the nylon-12 polymer and increased radiopacity when subjected to X-ray imaging relative to the original polymer.

In a further illustrative embodiment Pebax® 7033 (0.5 g) may be dissolved in 10 ml DMAC in a 50 ml R.B. flask. The acid chloride of N-(2,6-diiodocarboxyphenyl)-3,4,5-triiodobenzamide (0.5 g), dissolved in 10 ml DMAC, is then added and the mixture heated at 150° C. for 12-24 hrs blanketed with dry nitrogen or argon. The polymer may then be concentrated, precipitated with methanol, and dried. The resulting polymer will have pendant iodoarylcarboxyl groups of the structure:

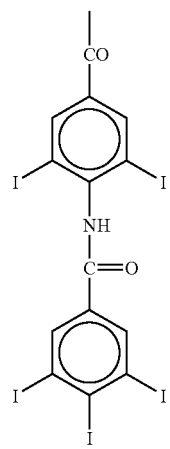

bound to nitrogen atoms in the polyamide block of the polymer and increased radiopacity when subjected to X-ray imaging relative to the original polymer.

In US 2005/0106119, US 2006/0024266, US 2006/0034769 and US 2006/0036316, there are described radiopaque polymers having iodine or bromine substituted aromatic groups in the main chain and in some cases amide groups in the main chain as well. Such polymers are said to be useful in various medical devices including embolotherapy products, stents, catheters, and the like. The polymers of the invention may be used in the same or substantially similar applications in the same manner as the polymers of these documents.

The medical device in accordance with the present invention may be an implantable or insertable medical device which is implanted or inserted either for procedural uses or as implants. Non-limiting examples include balloons, catheters (e.g., renal or vascular catheters such as balloon catheters, guide catheters and stent delivery systems), guide wires, needles, surgical instruments, dental devices, endoscopes, filters (e.g., vena cava filters), stents (including coronary artery stents, peripheral vascular stents such as cerebral stents, urethral stents, ureteral stents, biliary stents, tracheal stents, gastrointestinal stents and esophageal stents), stent delivery systems, stent grafts, vascular grafts, vascular access ports, embolization devices including cerebral aneurysm filler coils (including Guglilmi detachable coils and metal coils), myocardial plugs, wound drains, gastroenteric tubes, urethral inserts, laproscopic equipment, pacemaker leads, defibrillator leads, shunts such as arteriovenuous shunts, artificial hearts and heart assist pumps, heart valves, vascular valves, tissue bulking devices, sutures, suture anchors, anastomosis clips and rings, tissue staples and ligating clips, cannulae, orthopedic prostheses, joint prostheses, as well as various other medical devices that are adapted for implantation or insertion into the body.

The medical devices of the present invention include implantable and insertable medical devices that are used for diagnosis, for systemic treatment, or for the localized treatment of any tissue or organ. Non-limiting examples are tumors; organs including the heart, coronary and peripheral vascular system (referred to overall as "the vasculature"), the urogenital system, including kidneys, bladder, urethra, ureters, prostate, vagina, uterus and ovaries, eyes, lungs, trachea, esophagus, intestines, stomach, brain, liver and pancreas, skeletal muscle, smooth muscle, breast, dermal tissue, cartilage, tooth and bone. As used herein, the term "diagnosis" refers to the act or process of determining the nature of a disease, condition or injury through examination and/or testing of a patient. As used herein, "treatment" refers to the prevention of a disease or condition, the reduction or elimination of symptoms associated with a disease, condition or injury, or the substantial or complete elimination of a disease, condition or injury. Typical subjects (also referred to as "patients") are vertebrate subjects, more typically mammalian subjects and even more typically human subjects.

The inventive polymer may be employed to form a component of such a medical device, which component may be a substructure of the device, for instance a catheter tip, marker band, or the like, or a coating or laminate layer, or in some cases the entire device. In the case of a coating or laminate layer the thickness of the polymer may be varied to provide a desired radioopacity. In the relevant device component, the polymer may be employed singly or in a blend with one or more other polymers to obtain a suitable balance of physical properties for the particular device component and desired radiopacity. The blend may include the parent amide polymer from which the inventive polymer was derived.

In particular embodiments the polymers of the invention are employed to form catheter tubing, catheter tips or catheter balloons. In such embodiments the inventive polymer may be optionally blended with the parent amide polymer as needed to provide a suitable balance of radiopacity and physical properties.

Polymers with which the inventive polymers may be laminated or blended include elastomeric and non-elastomeric polymers. Particular examples include polyesters, polyester block copolymers, polyamides, polyamide block copolymers, (meth)acrylic polymers and copolymers; polyethers; polyimides; polycarbonates; polyacrylonitriles; polymers and copolymers of vinyl monomers including styrenic monomers, and various block copolymers of such monomers; polyolefin polymers and copolymers; fluorinated polymers and copolymers; silicone polymers and copolymers; polyurethanes; biopolymers, such as polypeptides, proteins, polysaccharides and fatty acids (and esters thereof), and the like.

As coating materials, or as components of coating compositions, the polymers of the invention may be applied to polymeric, metal and/or ceramic substrates. Coatings may be applied in any conventional manner, for instance from solution, dispersion or melt by spraying, brushing, dipping, or the like, and also as powder coatings.

Polymers of the invention may also be formulated into polymer/ceramic hybrid materials, for instance by mixing polymer solutions or dispersions with sol-gel ceramic precursor materials or solutions containing such sol-gel ceramic precursor materials as described in U.S. application Ser. No. 11/094638, filed Mar. 30, 2005. The sol-gel ceramic precursor materials used are typically inorganic metallic and semi-metallic salts, metallic and semi-metallic complexes/chelates (e.g., metal acetylacetonate complexes), metallic and semi-metallic hydroxides, or organometallic and organo-semi-metallic compounds (e.g., metal alkoxides and silicon alkoxides and acyloxides). In a typical sol-gel process, precursor materials such as those described above are subjected to hydrolysis and condensation (also referred to as polymerization) reactions to form a colloidal suspension, or "sol." For example, an alkoxide of choice (such as a methoxide, ethoxide, isopropoxide, tert-butoxide, etc.) of a semi-metal or metal of choice (such as silicon, aluminum, zirconium, titanium, tin, hafnium, tantalum, molybdenum, tungsten, rhenium, iridium, etc.) may be dissolved in a suitable solvent, for example, in one or more alcohols and subjected to hydrolysis and condensation, for example, by adding water or another aqueous solution, such as an acidic or basic aqueous solution to form a sol. The mixture is further processed by drying. A ceramic oxide network of the selected semi-metal or metal atoms is produced. To form hybrid materials a solution of a polymer of the invention may be incorporated into the initial solution of the sol-gel ceramic precursor or added at the sol stage.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to." Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all claims which possess all antecedents referenced in such dependent claim if such multiple dependent format is an accepted format within the jurisdiction. In jurisdictions where multiple dependent claim formats are restricted, the following dependent claims should each be also taken as alternatively written in each singly dependent claim format which creates a dependency from an antecedent-possessing claim other than the specific claim listed in such dependent claim.

The invention claimed is:

1. A polymer, having a main chain and a plurality of amide groups wherein at least some of the amide groups have, bound to the amide nitrogen atom thereof, an organohalide group that is pendant to the polymer main chain, the organohalide groups comprising one or more iodine and/or bromine atoms thereon which is a poly(ether-block-amide).

2. A polymer having a main chain and a plurality of amide groups and having amide groups in the main chain segment wherein at least some of the amide groups have, bound to the amide nitrogen atom thereof, an organohalide group that is pendant to the polymer main chain, the organohalide groups comprising one or more iodine and/or bromine atoms thereon and said organohalide groups being side chain moieties bond to nitrogen atoms of the main chain segment amide groups by a carbon-nitrogen bond.

3. A polymer having a main chain and a plurality of amide groups wherein at least some of the amide groups have, bound to the amide nitrogen atom thereof, an organohalide group that is pendant to the polymer main chain, the organohalide groups comprising one or more iodine and/or bromine atoms thereon wherein the organohalide group has the formula:

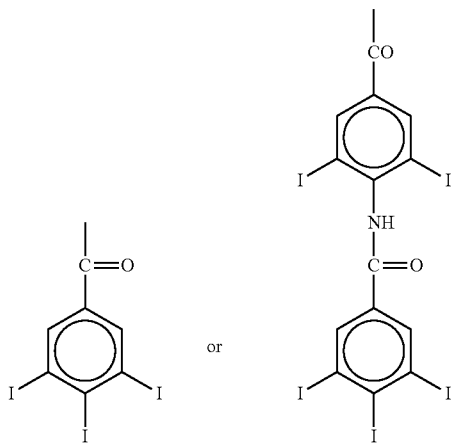

and the polymer is a poly(ether-block-amide) (PEBA).

4. A polymer as in claim 3 wherein the PEBA polymer comprises ester linkages between polyamide and polyether segments.

5. A medical device comprising a component formed of a polymer having a main chain and a plurality of amide groups wherein at least some of the amide groups have, bound to the amide nitrogen atom thereof, an organohalide group that is pendant to the polymer main chain, the organohalide groups comprising one or more iodine and/or bromine atoms thereon.

6. A medical device as in claim 5 wherein the medical device is a member of the group consisting of balloons, catheters, guide wires, needles, surgical instruments, dental devices, endoscopes, filters, stents, stent delivery systems, stent grafts, vascular grafts, vascular access ports, embolization devices, myocardial plugs, wound drains, gastroenteric tubes, urethral inserts, laproscopic equipment, pacemaker leads, defibrillator leads, shunts, artificial hearts and heart assist pumps, heart valves, vascular valves, tissue bulking devices, sutures, suture anchors, anastomosis clips and rings, tissue staples and ligating clips, cannulae, orthopedic prostheses, and joint prostheses.

7. A medical device as in claim 5 wherein said component is a polymer coating.

8. A polymer/ceramic hybrid material comprising a polymer having a main chain and a plurality of amide groups wherein at least some of the amide groups have, bound to the amide nitrogen atom thereof, an organohalide group that is pendant to the polymer main chain, the organohalide groups comprising one or more iodine and/or bromine atoms thereon, and a ceramic comprising an oxide-linked network of one or more members of the group consisting of silicon, aluminum, zirconium, titanium, tin, hafnium, tantalum, molybdenum, tungsten, rhenium, and iridium.

9. A medical device as in claim 6, wherein the medical device is a balloon.

* * * * *